United States Patent
Wang et al.

(10) Patent No.: US 11,707,551 B2
(45) Date of Patent: Jul. 25, 2023

(54) IMPLANT SHREDDER AND IMPLANT FORMING METHOD

(71) Applicant: METAL INDUSTRIES RESEARCH & DEVELOPMENT CENTRE, Kaohsiung (TW)

(72) Inventors: Yue-Jun Wang, New Taipei (TW); Chun-Chieh Tseng, Kaohsiung (TW); Tung-Lin Tsai, Tainan (TW)

(73) Assignee: METAL INDUSTRIES RESEARCH & DEVELOPMENT CENTRE, Kaohsiung (TW)

( * ) Notice: Subject to any disclaimer, the term of this patent is extended or adjusted under 35 U.S.C. 154(b) by 51 days.

(21) Appl. No.: 17/506,866

(22) Filed: Oct. 21, 2021

(65) Prior Publication Data
US 2023/0131187 A1  Apr. 27, 2023

(51) Int. Cl.
*A47J 42/24*  (2006.01)
*A47J 42/32*  (2006.01)
(Continued)

(52) U.S. Cl.
CPC ...... *A61L 27/3691* (2013.01); *A61F 2/30756* (2013.01); *A61F 2/30942* (2013.01);
(Continued)

(58) Field of Classification Search
CPC .. A47J 42/24; A47J 42/32; A47J 42/34; A61F 2/30942; A61F 2002/30943;
(Continued)

(56) References Cited

U.S. PATENT DOCUMENTS 4,014,971 A * 3/1977 Perkins ............... A61L 27/3683
264/219 X
5,741,215 A * 4/1998 D'Urso ............... A61F 2/30942
600/407
(Continued)

FOREIGN PATENT DOCUMENTS

CN   108325671 A   7/2018
CN   208852962 U   5/2019
(Continued)

OTHER PUBLICATIONS

Translation of DE 202010000512 U1 (published on Aug. 10, 2011).*

*Primary Examiner* — Leo B Tentoni
(74) *Attorney, Agent, or Firm* — Alan D. Kamrath; Karin L. Williams; Mayer & Williams PC (57) ABSTRACT

An implant shredder includes a base and a cutting member. The base includes a first chamber and a second chamber intercommunicating with the first chamber. The first chamber includes an inlet. The second chamber includes an outlet. The cutting member is received in the second chamber. The cutting member is driven by a driving member to rotate. The cutting member includes a plurality of cutting edges located on a circumference of a same radius. The plurality of cutting edges is rotatably disposed adjacent to a location intercommunicating with the first chamber. An implant forming method includes creating data of an outline of an implant; producing a shaping mold based on the data; and cutting a to-be-processed object with the implant shredder, then mixing the to-be-proceed object with a biological tissue glue to obtain a raw material, and filling the raw material into the shaping mold to form the implant.

20 Claims, 5 Drawing Sheets

(51) Int. Cl.
    *A47J 42/34*     (2006.01)
    *B29C 64/112*     (2017.01)
    *B33Y 10/00*     (2015.01)
    *A61L 27/36*     (2006.01)
    *B02C 18/14*     (2006.01)
    *B02C 18/24*     (2006.01)
    *B02C 18/22*     (2006.01)
    *A61F 2/30*     (2006.01)
    *B29C 33/38*     (2006.01)
    *B33Y 80/00*     (2015.01)
    *B29C 69/00*     (2006.01)
    *B29C 64/106*     (2017.01)
    *B29L 31/00*     (2006.01)

(52) U.S. Cl.
CPC ........ *A61L 27/3612* (2013.01); *B02C 18/145* (2013.01); *B02C 18/2233* (2013.01); *B02C 18/24* (2013.01); *B29C 33/3835* (2013.01); *B29C 33/3842* (2013.01); *B29C 69/001* (2013.01); *B33Y 80/00* (2014.12); *A61F 2002/30943* (2013.01); *A61F 2002/30952* (2013.01); *A61F 2002/30957* (2013.01); *B29C 64/106* (2017.08); *B29L 2031/7532* (2013.01); *G06T 2207/10081* (2013.01)

(58) Field of Classification Search
CPC .. A61F 2002/30944; A61F 2002/30952; A61F 2002/30957; B02C 18/145; B02C 18/2233; B02C 18/24; B29C 33/3842; B29C 45/001; B29C 64/106; B29C 64/112; B29C 69/001; B29L 2031/7532; B33Y 10/00; G06T 2207/10081
USPC ....... 264/140, 219, 308, 328.1, 330; 83/331; 164/15; 241/93, 169.1; 382/131; 700/97, 119, 146
See application file for complete search history.

(56) References Cited

U.S. PATENT DOCUMENTS

| | | | | |
|---|---|---|---|---|
| 6,318,651 | B1* | 11/2001 | Spiering | A61F 2/4644 241/93 X |
| 6,464,156 | B1* | 10/2002 | Wexell | A61F 2/4644 241/93 X |
| 2003/0036800 | A1* | 2/2003 | Meredith | A61L 27/3683 264/330 X |

FOREIGN PATENT DOCUMENTS

| | | | | |
|---|---|---|---|---|
| DE | 202010000512 U1 * | 8/2011 | ........ | B02C 18/145 |
| TW | M568105 U | 10/2018 | | |

* cited by examiner

A
IMPLANT SHREDDER AND IMPLANT FORMING METHOD

BACKGROUND OF THE INVENTION

1. Field of the Invention

The present invention relates to a shredder and a method for forming an object and, more particularly, to an implant shredder and an implant forming method.

2. Description of the Related Art

Among the implants for human bodies used in medical treatments, autologous cartilage implants have advantages of avoidance of tissue rejection, low infection rate, and natural feel and are, thus, widely used in plastic surgery. Before implantation into a human body, the cartilage is cut into particles. Then, a tissue glue is used to coagulate and shape the cartilage particles.

However, cutting the cartilage into particles requires a doctor to manually hold a conventional cutter for cutting purposes, which increases the operation time, rendering the operation procedure laborious and time-consuming. Furthermore, the implant formed by the cartilage requires manual shaping based on the experience of the doctor during surgery. Thus, the probability of error of the outline of the implant due to human factor is still high.

Thus, it is necessary to improve the conventional cutter for cutting cartilage and the implant forming method.

SUMMARY OF THE INVENTION

It is therefore an objective of the present invention to provide an implant shredder for saving the time for cutting the implant.

It is another objective of the present invention to provide an implant forming method to avoid inconsistent outline of the implant due to human factor.

As used herein, the term "a", "an" or "one" for describing the number of the elements and members of the present invention is used for convenience, provides the general meaning of the scope of the present invention, and should be interpreted to include one or at least one. Furthermore, unless explicitly indicated otherwise, the concept of a single component also includes the case of plural components.

As used herein, the term "coupling", "engagement", "assembly", or similar terms is used to include separation of connected members without destroying the members after connection or inseparable connection of the members after connection. A person having ordinary skill in the art would be able to select according to desired demands in the material or assembly of the members to be connected.

An implant shredder according to the present invention includes a base and a cutting member. The base includes a first chamber and a second chamber intercommunicating with the first chamber. The first chamber includes an inlet. The second chamber includes an outlet. The cutting member is received in the second chamber. The cutting member is configured to be driven by a driving member to rotate. The cutting member includes a plurality of cutting edges located on a circumference of a same radius. The plurality of cutting edges is rotatably disposed adjacent to a location intercommunicating with the first chamber.

An implant forming method according to the present invention includes creating data of an outline of an implant; producing a shaping mold based on the data; and cutting a to-be-processed object with the implant shredder, then mixing the to-be-proceed object with a biological tissue glue to obtain a raw material, and filling the raw material into the shaping mold to form the implant.

Thus, the implant shredder according to the present invention uses the driving member to drive the plurality of cutting edges to rotate, such that the to-be-processed object can be simultaneously cut by the plurality of cutting edges. Thus, the to-be-processed object can be rapidly and effortlessly shredded into particles, saving the time for cutting. According to the implant forming method according to the present invention, the outline of the implant can be ascertained by the shaping mold, such that a doctor can accurately and rapidly shape the implant, avoiding inconsistent implant outline due to human factor.

In an example, the second chamber has circular cross sections defined by an inner periphery of a peripheral wall of the second chamber, and the plurality of cutting edges is rotatable along the inner periphery of the peripheral wall of the second chamber. Thus, the base and the cutting member can be assembled conveniently.

In an example, the base includes at least one holding portion extending outward from an outer periphery of the base. Thus, a worker can conveniently hold the implant shredder to proceed with processing of the to-be-processed object.

In an example, the at least one holding portion includes two holding portions disposed on two opposite sides of the base. Thus, a user can stably hold the base with two fingers.

In an example, the base includes a pressing member movable in the first chamber. Thus, the pressing member can push the to-be-processed object to contact with the plurality of cutting edges of the cutting member, fully cutting the to-be-processed object.

In an example, the outlet includes a coupling portion coupled with a cap. Thus, the cutting member is prevented from disengaging from the second chamber.

In an example, the implant shredder further includes a container having a third chamber. The container is connected to the outlet of the base via the coupling portion and the cap. Thus, after being shredded into particles, the to-be-processed can be received in the third chamber for easy removal.

In an example, the container includes an injection port intercommunicating with the third chamber. Thus, the to-be-processed object shredded into particles and received in the third compartment can be conveniently filled into the shaping mold, providing use convenience.

In an example, the driving member is L-shaped, and an end of the driving member is coupled to an end face of the cutting member. Thus, the driving member can directly drive the cutting member.

In an example, another end of the driving member includes a gripping portion for driving the cutting member to rotate. Thus, the cutting member can be driven by gripping the gripping portion.

In an example, the plurality of cutting edges and the gripping portion rotate about a same axis. The plurality of cutting edges and the axis are spaced from each other by a first radius of rotation. The gripping portion and the axis are spaced from each other by a second radius of rotation. The second radius of rotation is at least four times the first radius of rotation. Thus, the driving member can apply a larger torque to drive the cutting member to rotate and cut, achieving an effort-saving effect.

In an example, the cutting member define a hollow cylinder having a peripheral wall. The peripheral wall of the hollow cylinder defined by the cutting member includes a plurality of through-holes. Each of the plurality of cutting edges is located on a portion of a peripheral edge of a respective one of the plurality of through-holes. Each of the plurality of cutting edges protrudes beyond an annular periphery of the cutting member. Thus, the plurality of cutting edges can be located on the circumference of the same radius for cutting purposes.

In an example, each of the plurality of through-holes has a diameter of 0.7-1.5 mm. Thus, the to-be-processed object can be cut into particles with suitable diameters, providing better formability and settability.

In an example, the plurality of through-holes has a same diameter. Thus, the to-be-processed object can be shredded into particles of the same diameter.

In an example, the cutting member includes two ends opposite to each other in an axial direction. One of the two ends of the cutting member has a connecting portion. The connecting portion is coupled to an end of the driving member extending through a through-hole of the base. Thus, the driving member can be directly coupled to the cutting member.

In an example, the data is created by micro-computed tomography scanning. Thus, the conditions of the outline of the implant can be estimated accurately.

In an example, the data of the outline of the implant is stored in a cloud database. Thus, the cloud database has a large volume, is highly reliable, and can be accessed conveniently, thereby safely storing the data.

In an example, the shaping mold is produced from 3D printing, computer numerical control machining, or injection molding. Thus, the shaping mold can be produced conveniently.

In an example, the shaping mold is made of polylactic acid (PLA), γ-polyglutamic acid (PGA), polycaprolactone (PLC), stainless steel, or titanium alloy. Thus, since polylactic acid (PLA), γ-polyglutamic acid (PGA) and polycaprolactone (PLC) are bio-degradable, environmental pollution can be avoided. Furthermore, since stainless steel and titanium alloy have higher mechanical strength, deformation of the shaping mold can also be avoided.

In an example, the shaping mold includes at least one filling port and at least one gas exhaust port. The at least one filling port and the at least one gas exhaust port intercommunicate with a cavity of the shaping mold. Thus, the to-be-processed object shredded into particles can be filled into the cavity of the shaping mold via the at least one filling port, and the gas remaining in the cavity can be discharged via the at least one gas exhaust port.

BRIEF DESCRIPTION OF THE DRAWINGS

The present invention will become more fully understood from the detailed description given hereinafter and the accompanying drawings which are given by way of illustration only, and thus are not limitative of the present invention, and wherein.

In the various figures of the drawings, the same numerals designate the same or similar parts. Furthermore, when the terms "inner", "outer", "top", "bottom", "front", "rear" and similar terms are used hereinafter, it should be understood that these terms have reference only to the structure shown in the drawings as it would appear to a person viewing the drawings, and are utilized only to facilitate describing the invention.

DETAILED DESCRIPTION OF THE INVENTION

Figure 1:
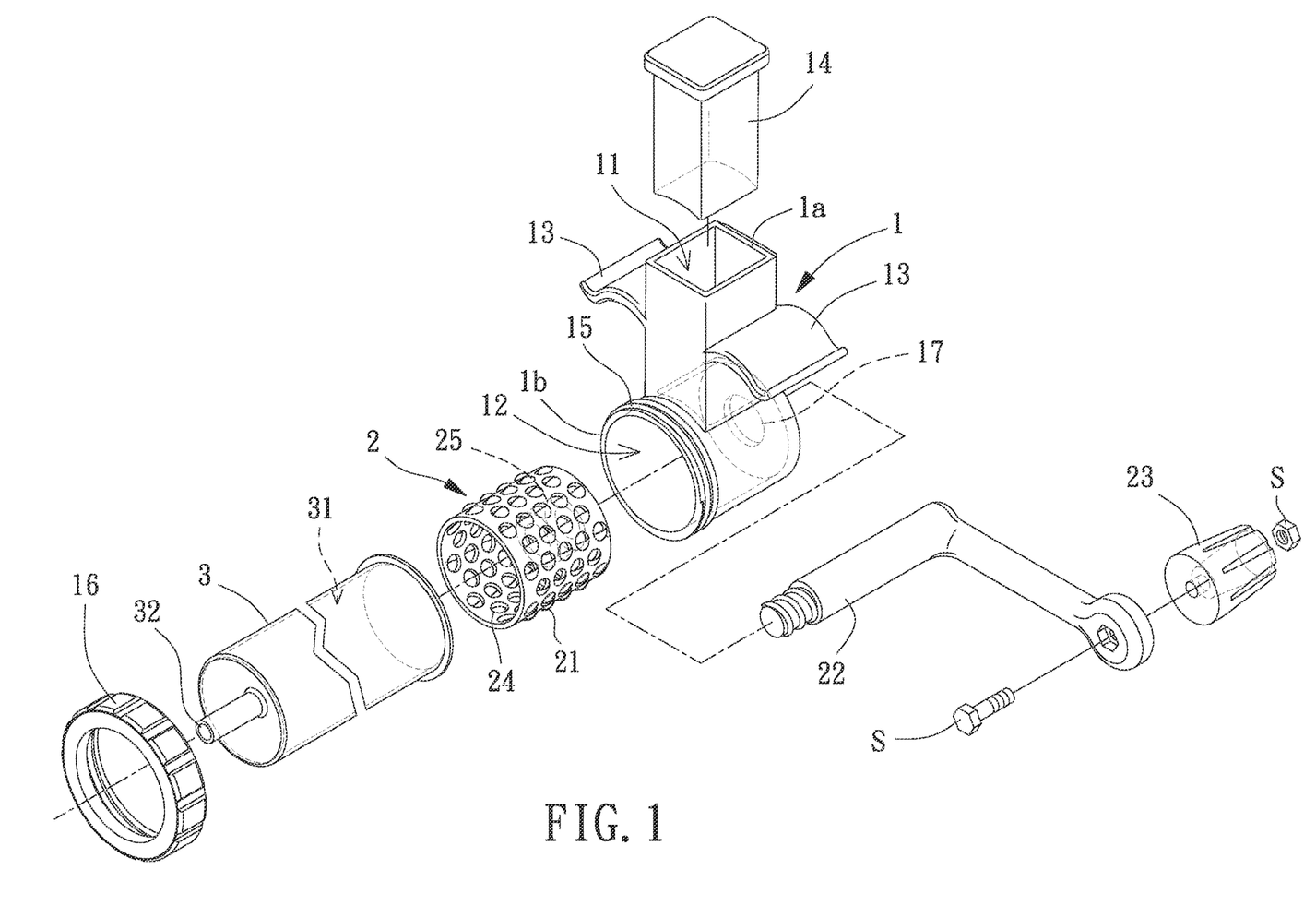
FIG. 1 is an exploded, perspective view of an implant shredder of an embodiment according to the present invention.

With reference to FIG. 1, an implant shredder of an embodiment according to the present invention includes a base 1 and a cutting member 2. The cutting member 2 is coupled to the base 1.

The base 1 includes a first chamber 11 and a second chamber 12 intercommunicating with the first chamber 11. The shape of cross-sections of the first chamber 11 is not limited in this invention. The cross sections of the second chamber 12 are preferably circular. The first chamber 11 includes an inlet 1a. The second chamber 12 includes an outlet 1b. Preferably, the base 1 includes at least one holding portion 13 extending outward from an outer periphery of the base 1. Preferably, the base 1 includes two holding portions 13 disposed on two opposite sides of the base 1. Furthermore, the base 1 includes a pressing member 14 movable in the first chamber 11.

The cutting member 2 is received in the second chamber 12 and is configured to be driven by a driving member 22. Preferably, the outlet 1b includes a coupling portion 15. The coupling portion 15 can be coupled with a cap 16 for limiting the rotation of the cutting member 2 in the second chamber 12. The coupling can be conventional threading connection. The cutting member 2 includes a plurality of cutting edges 21 located on a circumference of the same radius. Thus, the plurality of cutting edges 21 can be rotatably disposed adjacent to a location intercommunicating with the first chamber 11. Alternatively, the plurality of cutting edges 21 can be rotatable along an inner periphery of a peripheral wall of the second chamber 12 which define circular cross sections. The driving member 22 can be a driving mechanism, such as a knob or a crank. In this embodiment, the driving member 22 is an L-shaped crank. An end of the driving member 22 can be coupled to an end face of the cutting member 2. Another end of the driving member 22 has a gripping portion 23 for driving the cutting member 2 to rotate. The gripping portion 23 can be fixed to the driving member 22. Alternatively, the gripping portion 23 can be coupled to the driving member 22 by conventional fasteners S, such that the gripping portion 23 can rotate relative to the driving member 22.

Figure 2:
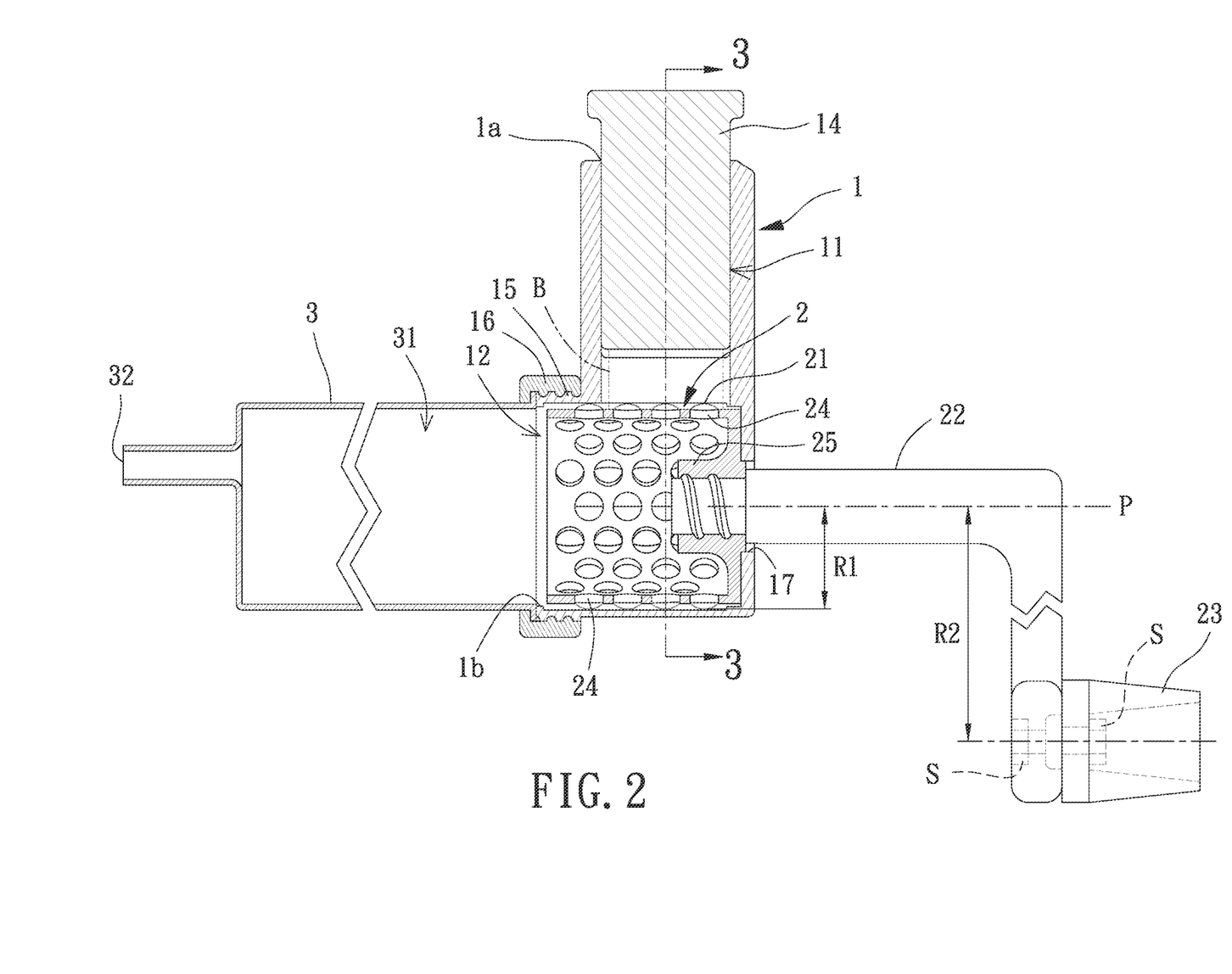
FIG. 2 is a cross-sectional view of the implant shredder of FIG. 1 after assembly.

With reference to FIGS. 1 and 2, in this embodiment, the cutting member 2 received in the second chamber 12 can be in the form of a hollow cylinder. A peripheral wall of the hollow cylinder formed by the cutting member 2 includes a plurality of through-holes 24. Each of the plurality of through-holes 24 has a diameter of 0.7-1.5 mm. The diameters of the plurality of through-holes 24 can be the same or different. Each of the plurality of cutting edges 21 is located on a portion of a peripheral edge of a respective one of the plurality of through-holes 24. Furthermore, each of the plurality of cutting edges 21 protrudes beyond an annular periphery of the cutting member 2. Thus, when the cutting member 2 rotates, each of the plurality of cutting edges 21 can shred a to-be-processed object B (such as cartilage) falling from the first chamber 11. The cutting member 2 has two ends opposite to each other in an axial direction. One of the two ends of the cutting member 2 has a connecting portion 25. The connecting portion 25 is coupled to an end of the driving member 22 extending through a through-hole 17 of the base 1. Preferably, the through-hole 17 is an axial hole.

With reference to FIG. 2, the plurality of cutting edges 21 and the gripping portion 23 rotate about the same axis P. The plurality of cutting edges 21 and the axis P are spaced from each other by a first radius of rotation R1. The gripping portion 23 and the axis P are spaced from each other by a second radius of rotation R2. Preferably, the second radius of rotation R2 is at least four times the first radius of rotation R1.

The implant shredder according to the present invention can further includes a container 3 which can be in the form of a barrel of a syringe. The container 3 includes a third chamber 31. The container 3 can be connected to the outlet 1b of the base 1 via the coupling portion 15 and the cap 16. Thus, the particles obtained from cutting the to-be-processed object B and falling onto the cutting member 2 may enter the third chamber 31. The container 3 further includes an injection port 32 intercommunicating with the third chamber 31.

Figure 3:
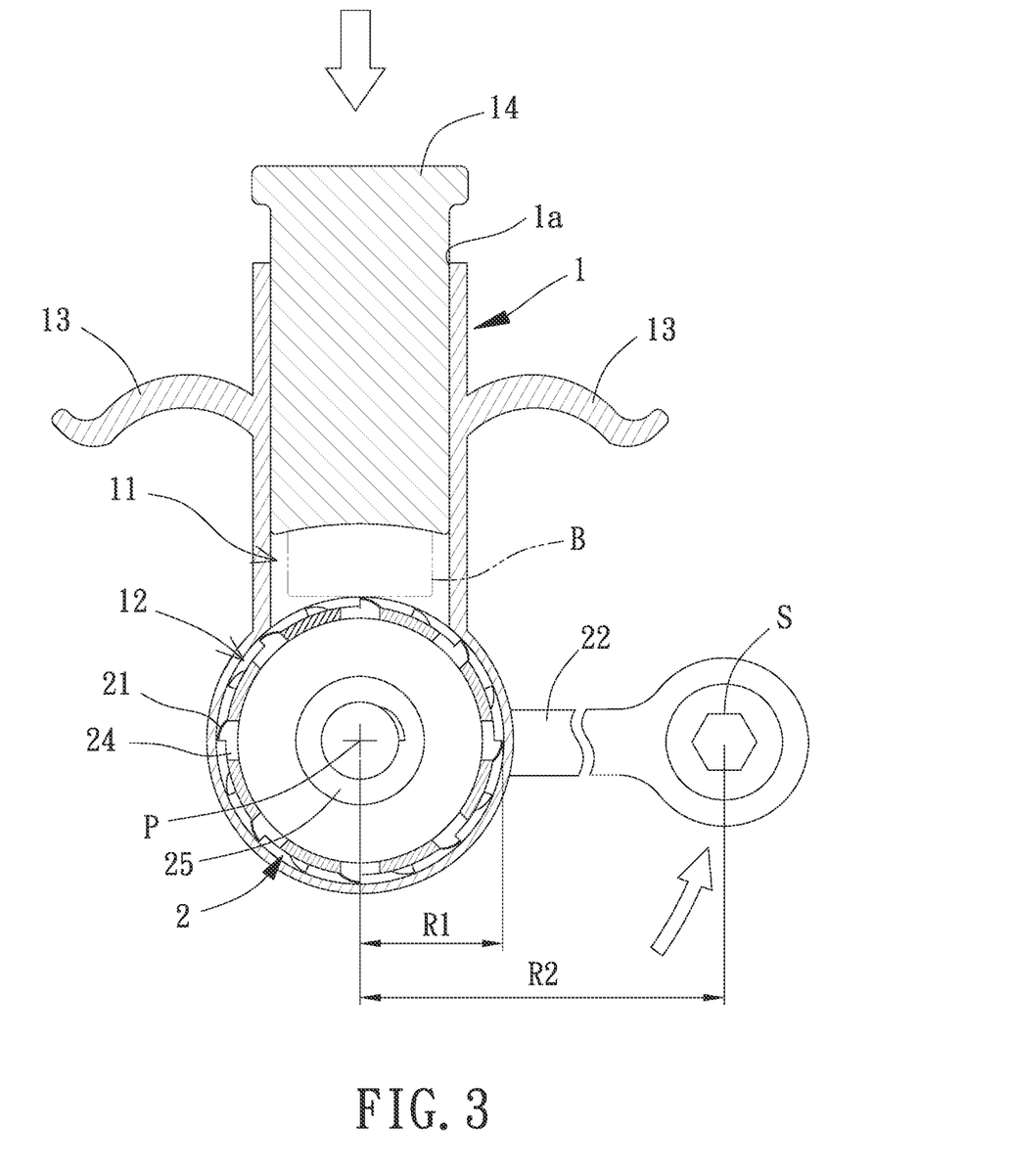
FIG. 3 is a cross sectional view taken along section line 3-3 of FIG. 2.

With reference to FIG. 3, the implant shredder can be used to cut the to-be-processed object B, such as a cartilage. Specifically, a user can place the to-be-processed object B into the first chamber 11 via the inlet 1a of the base 1, and the driving member 22 is used to drive the cutting member 2 to rotate, such that the plurality of cutting edges 21 cuts the to-be-processed object B into particles which fall into the cutting member 2. When the plurality of through-holes 24 of the cutting member 2 has the same diameter, the to-be-processed object B can be shredded into particles of the same diameter.

If necessary, the pressing member 14 can be used to push the to-be-processed object B. Furthermore, the user can hold the base 1 by two fingers gripping the two holding portions 13 and can use the thumb to push the pressing member 14, which, in turn, pushes the to-be-processed object B to come into contact with the plurality of cutting edges 21 of the cutting member 2. Thus, the implant shredder can be conveniently used by the user. The user can use the driving member 22 to drive the cutting member 2 to rotate, such that the plurality of cutting edges 21 can cut the to-be-processed object B. Since to-be-processed object B can be simultaneously cut by the plurality of cutting edges 21, the user can rapidly and effortlessly shred the to-be-processed object B into particles. When the plurality of through-holes 24 of the cutting member 2 has the same diameter, the to-be-processed object B can be shredded into particles of the same diameter. Furthermore, when the second radius of rotation R2 of the driving member 22 is at least four times the first radius of rotation R1 of the plurality of cutting edges 21, the user can conveniently use a larger torque to cut the to-be-processed object B.

The to-be-processed object B which is shredded into particles falls into the third chamber 31 of the container 3. After collecting the particles of the to-be-processed object B, the container 3 can be separated from the base 1. Thus, the user can directly and conveniently add a shaping agent which is biocompatible and absorbable. The shaping agent can be a biological tissue glue and can be used to coagulate the particles of the to-be-processed object B.

Figure 4:
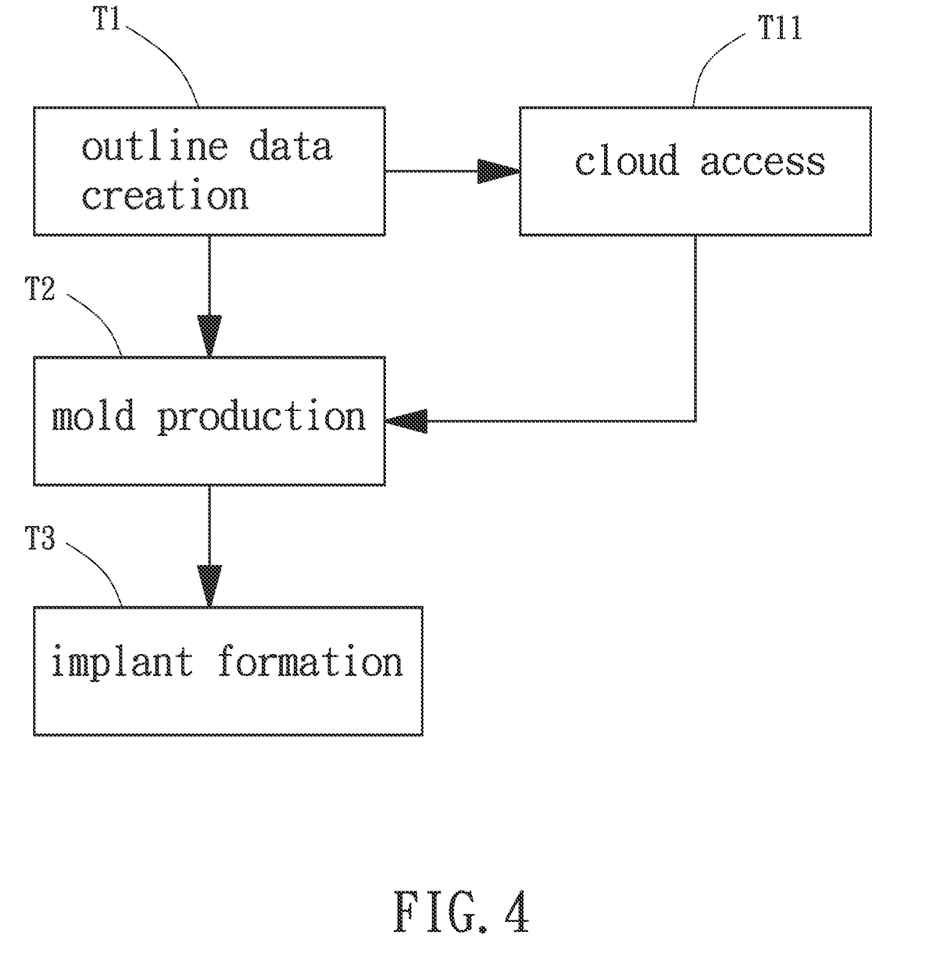
FIG. 4 is a flowchart illustrating an implant forming method according to the present invention.
Figure 5:
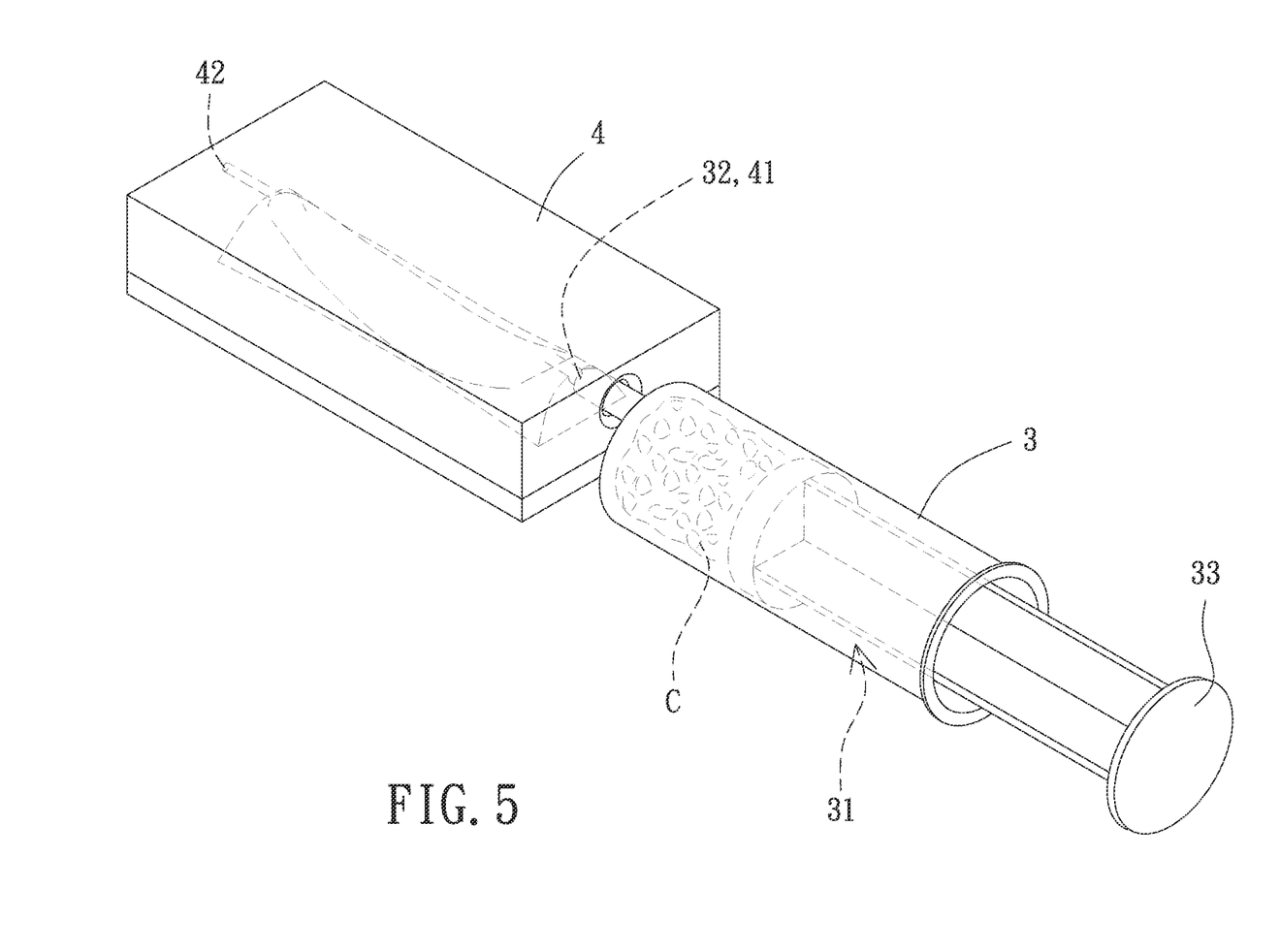
FIG. 5 is a perspective view illustrating shaping of an outline of an implant through use of a shaping mold.

With reference to FIGS. 4 and 5, a raw material C is obtained after the particles of the to-be-processed object B are mixed with the shaping agent. An implant forming method can be used to form an implant from the raw material C. The implant forming method includes an outline data creation step (step T1), a mold production step (step T2), and an implant formation step (step T3).

More specifically, the outline data creation step T1 includes creation of data of an outline of an implant. The outline data creation step T1 can be carried out by a doctor. According to the affected region of a patient, the doctor can estimate the outline conditions, such as the shape, size, and angle of the implant. The conditions of the outline are converted into the data. For example, the data can be created by a doctor using micro-computed tomography (Micro-CT) to scan the affected region of the patient. Thus, the conditions of the outline can be estimated accurately.

Preferably, a cloud access step T11 can be carried out after the outline data creation step T1. The cloud access step T11 can store the data in a cloud database which has advantages of large volume, high reliability, and easy access, such that the data can be well stored.

The mold production step T2 includes producing a shaping mold based on the data. For example, a doctor can send the data of the implant outline to a mold manufacturer directly or through the cloud database. Based on the data, the mold manufacturer can reproduce the mold through computer operation to establish figure files for processing molds. The shaping mold can be produced from 3D printing, computer numerical control (CNC) machining, or injection molding. The shaping mold can be made of polymers without biological toxicity, such as polylactic acid (PLA), γ-polyglutamic acid (PGA) or polycaprolactone (PCL). The shaping mold can also be made of stainless steel or titanium alloy. The present invention is not limited in this regard.

With reference to FIG. 5, the implant formation step T3 includes filling the raw material C (the to-be-processed object B after cutting) into the shaping mold 4 to form the implant. The shaping mold 4 includes at least one filling port 41 and at least one gas exhaust port 42. The at least one filling port 41 and the at least one gas exhaust port 42 intercommunicate with a cavity of the shaping mold 4. The injection port 32 of the container 3 intercommunicates with the at least one filling port 41. The container 3 can be coupled with a pushing member 33. The pushing member 33 can be a plunger of a syringe. The pushing member 33 can push the raw material C in the third chamber 31 into the at least one filling port 41 and then into the cavity of the shaping mold 4. Thus, the raw material C can be filled into the cavity of the shaping mold 4. During the filling process, the at least one gas exhaust port 42 can be used to discharge the gas remaining in the cavity, avoiding incomplete filling of the raw material C. The raw material C stands a period of time after filling, and the implant can be removed for use after formation. Since the doctor can ascertain the outline of the implant by the shaping mold 4, the implant can be rapidly and conveniently formed. In an alternative embodiment, the raw material C can be filled into a female mold of the shaping mold 4 and then pressed by a male mold of the shaping mold 4 to take shape, which can be appreciated by one having ordinary skill in the art.

In view of the foregoing, the implant shredder according to the present invention uses the driving member to drive the plurality of cutting edges to rotate, such that the to-be-processed object can be simultaneously cut by the plurality of cutting edges. Thus, the to-be-processed object can be rapidly and effortlessly shredded into particles, saving the time for cutting. According to the implant forming method according to the present invention, the outline of the implant can be ascertained by the shaping mold, such that a doctor can accurately and rapidly shape the implant, avoiding inconsistent implant outline due to human factor.

Although the invention has been described in detail with reference to its presently preferable embodiments, it will be understood by one of ordinary skill in the art that various modifications can be made without departing from the spirit and the scope of the invention, as set forth in the appended claims.

What is claimed is:

1. An implant shredder comprising:
   a base including a first chamber and a second chamber intercommunicating with the first chamber, wherein the first chamber includes an inlet, and wherein the second chamber includes an outlet;
   a cutting member received in the second chamber, wherein the cutting member is configured to be driven by a driving member to rotate, wherein the cutting member includes a plurality of cutting edges located on a circumference of a same radius, and wherein the plurality of cutting edges is rotatably disposed adjacent to a location intercommunicating with the first chamber; and
   wherein the outlet includes a coupling portion coupled with a cap.

2. The implant shredder as claimed in claim 1, wherein the second chamber has circular cross sections defined by an inner periphery of a peripheral wall of the second chamber, and wherein the plurality of cutting edges is rotatable along the inner periphery of the peripheral wall of the second chamber.

3. The implant shredder as claimed in claim 1, wherein the base includes at least one holding portion extending outward from an outer periphery of the base.

4. The implant shredder as claimed in claim 3, wherein the at least one holding portion includes two holding portions disposed on two opposite sides of the base.

5. The implant shredder as claimed in claim 1, wherein the base includes a pressing member movable in the first chamber.

6. The implant shredder as claimed in claim 1, further comprising a container having a third chamber, wherein the container is connected to the outlet of the base via the coupling portion and the cap.

7. The implant shredder as claimed in claim 6, wherein the container includes an injection port intercommunicating with the third chamber.

8. The implant shredder as claimed in claim 1, wherein the driving member is L-shaped, and wherein an end of the driving member is coupled to an end face of the cutting member.

9. The implant shredder as claimed in claim 8, wherein another end of the driving member includes a gripping portion for driving the cutting member to rotate.

10. The implant shredder as claimed in claim 9, wherein the plurality of cutting edges and the gripping portion rotate about a same axis, wherein the plurality of cutting edges and the axis are spaced from each other by a first radius of rotation, wherein the gripping portion and the axis are spaced from each other by a second radius of rotation, and wherein the second radius of rotation is at least four times the first radius of rotation.

11. The implant shredder as claimed in claim 1, wherein the cutting member define a hollow cylinder having a peripheral wall, wherein the peripheral wall of the hollow cylinder defined by the cutting member includes a plurality of through-holes, wherein each of the plurality of cutting edges is located on a portion of a peripheral edge of a respective one of the plurality of through-holes, and wherein each of the plurality of cutting edges protrudes beyond an annular periphery of the cutting member.

12. The implant shredder as claimed in claim 11, wherein each of the plurality of through-holes has a diameter of 0.7-1.5 mm.

13. The implant shredder as claimed in claim 11, wherein the plurality of through-holes has a same diameter.

14. The implant shredder as claimed in claim 1, wherein the cutting member includes two ends opposite to each other in an axial direction, wherein one of the two ends of the cutting member has a connecting portion, and wherein the connecting portion is coupled to an end of the driving member extending through a through-hole of the base.

15. An implant forming method using an implant shredder set forth in claim 1, comprising:
   creating data of an outline of an implant;
   producing a shaping mold based on the data; and
   cutting a to-be-processed object with the implant shredder, then mixing the to-be-proceed object with a biological tissue glue to obtain a raw material, and filling the raw material into the shaping mold to form the implant.

16. The implant forming method as claimed in claim 15, wherein the data is created by micro-computed tomography scanning.

17. The implant forming method as claimed in claim 15, wherein the data of the outline of the implant is stored in a cloud database.

18. The implant forming method as claimed in claim 15, wherein the shaping mold is produced from 3D printing, computer numerical control machining, or injection molding.

19. The implant forming method as claimed in claim 15, wherein the shaping mold is made of polylactic acid (PLA), γ-polyglutamic acid (PGA), polycaprolactone (PLC), stainless steel, or titanium alloy.

20. The implant forming method as claimed in claim 15, wherein the shaping mold includes at least one filling port and at least one gas exhaust port, and wherein the at least one filling port and the at least one gas exhaust port intercommunicate with a cavity of the shaping mold.

* * * * *